(12) United States Patent
Yu

(10) Patent No.: US 6,404,489 B1
(45) Date of Patent: Jun. 11, 2002

(54) INCLUSION DETECTION

(75) Inventor: C. Charles Yu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/538,717

(22) Filed: Mar. 29, 2000

(51) Int. Cl.$^7$ ............................................. G01N 21/88
(52) U.S. Cl. ................................................. 356/239.1
(58) Field of Search ........................... 356/239.1, 239.2

(56) References Cited

U.S. PATENT DOCUMENTS

| | | | |
|---|---|---|---|
| 552,641 A | * | 1/1896 | Hoskins .................... 356/237.1 |
| 4,136,961 A | | 1/1979 | Young, II ..................... 356/239 |
| 4,808,813 A | * | 2/1989 | Champetier ................. 356/124 |
| 5,355,213 A | * | 10/1994 | Dotan ...................... 356/239.7 |
| 5,627,638 A | * | 5/1997 | Vokhmin ..................... 356/338 |
| 5,691,811 A | | 11/1997 | Kihira ........................ 356/237 |
| 5,790,247 A | * | 8/1998 | Henley et al. ............ 356/239.1 |
| 5,859,364 A | | 1/1999 | Toda et al. ..................... 73/105 |
| 5,894,345 A | | 4/1999 | Takamoto et al. ....... 356/237.1 |

* cited by examiner

Primary Examiner—Richard A. Rosenberger
(74) Attorney, Agent, or Firm—Timothy M. Schaeberle; Siwen Chen

(57) ABSTRACT

This light scattering technique for size measurement is based on the fact that an illuminated particle (inclusion) serves as a secondary radiation source in a manner which is related to its size. This technique allows for detection of inclusions in the interior of a transparent sheet. When illuminated with a beam of monochromatic light such as a laser beam as the primary light source, the angular distribution of the scattered intensity originated from the inclusion in the micron to submicron range, is a function of intensity, wavelength and index of refraction. The primary beam of light passes through the sheet on a straight line path parallel to a horizontal axis. A detector positioned at an angle to the horizontal axis detects the secondary scattered light.

20 Claims, 2 Drawing Sheets

INCLUSION DETECTION

TECHNICAL FIELD

This invention relates to a method and instrument design for detecting small inclusions in a transparent sheet. This invention uses a light trap in a unique way.

BACKGROUND ART

Detecting small (micron and submicron) inclusions in glass always has been a challenge. The difficulties associated with various practices are sensitivity, resolution, depth of focus, to name a few. Microscopy has the capability to detect inclusions down to the submicron range, yet it has an extremely narrow depth of focus and a small sampling area at high magnification. These are necessary for detecting small inclusions. If used alone, these restrictions make it next to impossible to analyze bulk glass. Diffused reflection/scattering has been used to identify inclusions. After mapping their location, the inclusion can be further determined by microscopy. Nevertheless, the detection limit for the diffused reflection/scattering approach is about 5 microns. In addition, the thickness of the glass is again somewhat restricted by the narrow depth of focus of the microscopy technique.

Small particles suspended in a fluid media, such as a liquid or gas, on the other hand, can be measured routinely by light scattering techniques. The differences between inclusions in a solid glass and particles suspended in a fluid are critical. One difference is that an inclusion in a glass is stationary. Its concentration level is normally very low, thus the signal intensity is so weak that it can hardly be distinguished from noise. Noise is the cross talk between surface detection (surface signals) and in depth detection (internal signals). In addition, the location of inclusions in glass would be valuable information. Due to the dynamic nature of the suspended particles in a fluid media, their location cannot be mapped. As a result, current existing instruments are not designed with particle location mapping capability. Nevertheless, we have found that the principle behind the measurement of particles suspended in fluid media is applicable for measurement of inclusions in solid glass.

DISCLOSURE OF INVENTION

My apparatus for detecting inclusions in a transparent sheet comprises in sequence a light source having a primary incident beam of light, at least one light trap and a transparent sheet. The transparent sheet has at least one exterior surface parallel to a horizontal axis and an interior depth with at least one inclusion therein. The inclusion intercepts the primary incident beam of light and creates a secondary radiation source forward scattered light. The light trap blocks the primary beam of light and prevents it from illuminating the exterior surface of the transparent sheet. The primary beam of light continues through the transparent sheet on a straight line path parallel to the horizontal axis and a detector position at an angle to the horizontal axis detects the secondary scattered light. Preferably, the angle is a 90° angle perpendicular to the horizontal axis. Typically, the transparent sheet has two exterior surfaces and the apparatus has two light traps that prevent the primary beam from illuminating the exterior surfaces of the transparent sheet.

We have found that the unique arrangement of the light traps prevents cross talk between surface signals and internal signals. This is especially true in the thinner sheets of transparent media. This arrangement allows for measuring the sheet in one pass, rather than the multiple passes required for bulk glass where noise is not as much of a problem.

Our light scattering technique for size measurement is based on the fact that an illuminated particle (or inclusion) serves as a secondary radiation source in a manner which is related to its size. When illuminated with a beam of monochromatic light using a laser beam as the primary light source the angular distribution of the scattered intensity originated from the inclusion in the micron to submicron range, is a function of the following. The angular distribution of the scattered intensity is a function of scattered light and the incident beam, the wavelength of the incident light, and the index of refraction of the particle relative to that of the surrounding media.

BESTMODE OF CARRYING OUT INVENTION

The transparent sheets we can measure may vary widely. Generally, the sheets may be any transparent glass, plastic, crystalline material, glass-ceramic and the like. Specifically, our big challenge was measuring inclusions in high purity fused silica (HPFS®) for photomask applications. We want to detect both gaseous and refractory inclusions in the HPFS®.

The transparency of the sheets may vary widely. Obviously, if the media is too translucent, the detection system will not be accurate. We have found that the media should have an internal transparency of at least 65%. Preferably, the transparency should be at least 90%.

A boule of HPFS® is roughly in the form of a disc about 60" in diameter and varies between 6" to 10" in thickness. For making 6" size photomask substrate, for example, the 60" diameter disc is first cut into about 6¼×6¼" square blocks of full thickness of the disc. Each block is then sliced into numerous plates of about ¼" thickness. The 6¼×6¼×¼ plates are lapped and then rough polished and subsequently fed through the inspection process.

Figure 1:
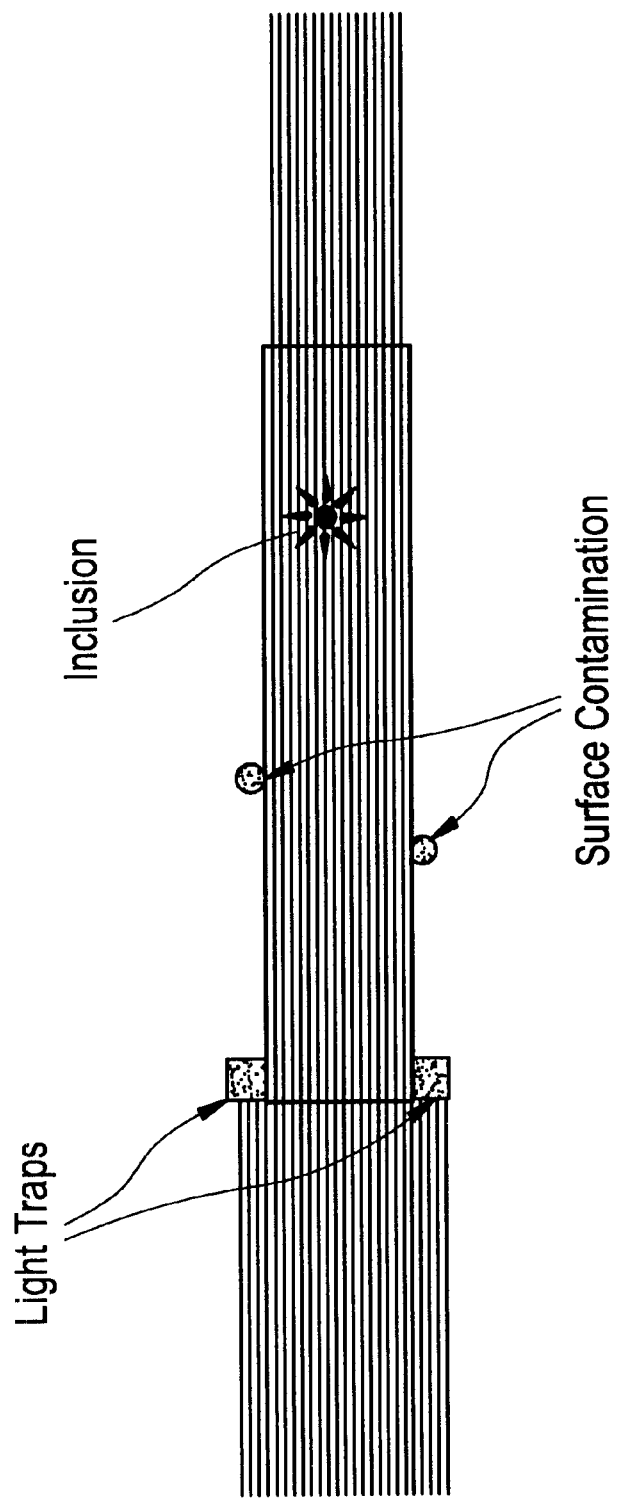
FIG. 1 illustrates the design principle of inclusion measurement for transparent sheets.

FIG. 1 is an illustration of a plate inspection. The expanded laser beam inspection system has found practical success in inspection HPFS® plates. The microscope based instruments have great difficulty in inspecting bulk glass due to narrow depth of field and field of view. By using collimated laser beam for illumination, the issue of limited depth of field is no longer a concern. By passing the laser beam throughout the entire plate in one sweep, not only can we easily detect inclusions deep inside, but we also generate an accurate 2-D inclusion map by noting the relative position of the inclusion along the laser beam and the relative position of the laser beam against the glass.

Figure 2:
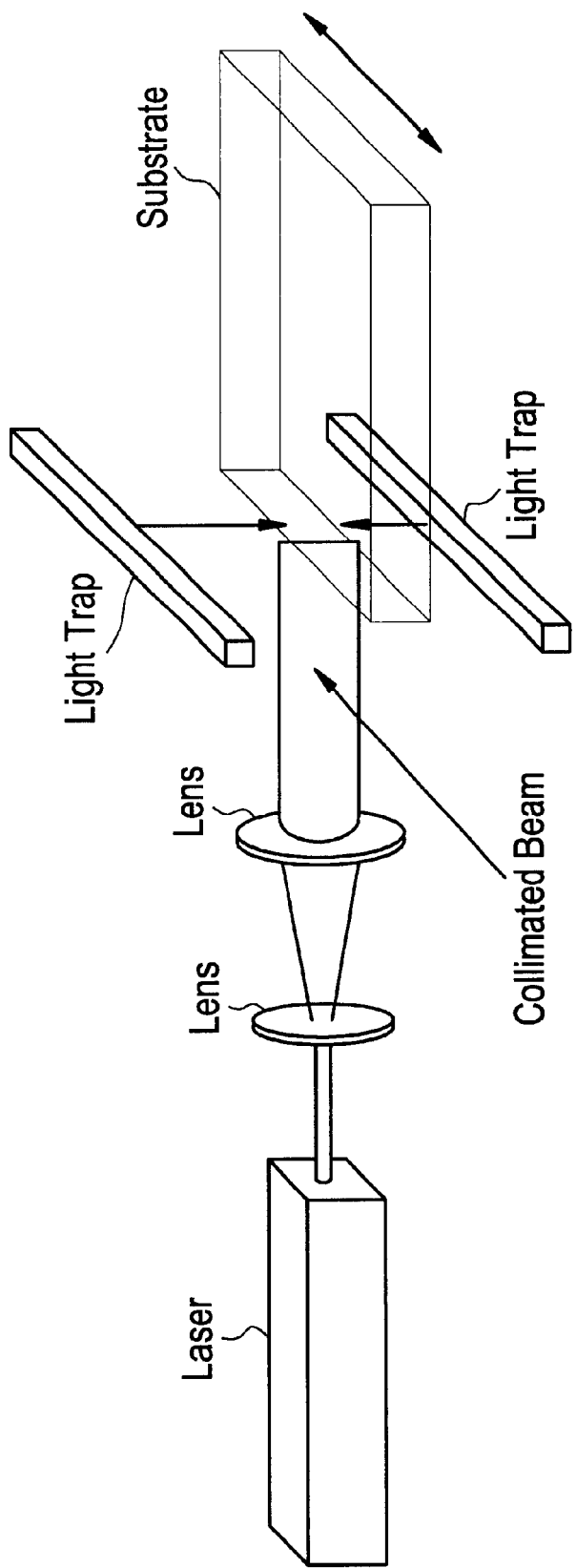
FIG. 2 is a schematic view of design set-up.

FIG. 2 shows that in the linear imaging approach, two detector array geometries are possible: single line, or multiple line detector array with time-delay-integration (TDI). TDI is a technique which improves signal-to-noise ration (SNR) by viewing the same object point with multiple-detector elements in a time sequence and co-adding all images of that point after the appropriate delay time. Because the signal is correlated for all elements while the noise for the same elements is uncorrelated, the SNR is improved by a factor of the square root of the number of elements. The TDI approach requires precise synchronization and timing control to achieve good results. In an imaging application where the best image is required, TDI offers very high image quality and sensitivity.

Calculations and measurements with the microprocessor shown in FIG. 2 indicate that we are well below the laser noise limit in the proposed configuration. A single row detector array was therefore selected as the detector element. The array provides a SNR of greater than 10 for a 1 micron particle illuminated by 35 mW laser diode at a wavelength of 660 nm. While this is a lower sensitivity than is obtainable with some TDI arrays, other features of the array make it a good choice for this application. The ultra-low lag characteristics allow higher scan speeds and better particle discrimination. In addition, because of its built-in timing generators and clock drivers, it is a relatively straightforward device to integrate into a complete detector assembly. A programmable shutter function provides for additional background discrimination and control.

Preferably, the detector is at a 90° angle to the horizontal axis (e.g. the path of the primary beam). Typically, the detector is at an angle ranging from 45° to 90°. If the angle is too shallow, the possibility for surface noise increases.

In addition to lasers, other possible illumination sources include halogen lamps and strobe lamps. Halogen and strobe lamps have the advantage of being non-coherent and are most useful in high magnification high resolution applications. In addition, halogen illuminators can achieve very high source stability for precise radiometric measurements. In the proposed system, however, optimum operation requires the use of a highly collimated small cross-section light beam. This is best achieved with a laser so that a near diffraction limited beam with a low divergence will equally illuminate inclusions across the full width of the sheet. A laser divergence will equally illuminate inclusions across the full width of the sheet. For best performance, a laser module with automatic power control (APC) circuitry and good thermal stability is required.

EXAMPLE

A boule of HPFS® is roughly in the form of a disc about 60" in diameter and varies between 6" to 10" in thickness. For making 6" size photomask substrate, for example, the 60" diameter disc is first cut into about 6¼×6¼ square blocks of full thickness of the disc. Each block is then sliced into numerous plates of about ¼" thickness. The 6¼"×6¼×¼" plates are lapped and then rough polished and subsequently fed through the inspection process.

The following is an example of our system used to detect potential inclusions in a photomask blank. One of the specifications of HPFS® fused silica to be used in photomask application is no inclusions above 2 micron (1 micron for high end applications) in size. Detection of small size inclusion in glass has always been a challenge. In one embodiment, the system consists of a 15 mW He—Ne Laser (wavelengths at 633 nm), and a beam expander with adjustable 2X~10X expansion capability. The light trap is made of black colored soft rubber.

The detector, a 2-D line scan camera, was positioned at a 90° angle perpendicular to the horizontal axis (e.g. perpendicular to the laser beam).

Inspection test result of using the prototype was very encouraging. The system showed the same, if not better, detection limit capability as that of the grid inspection approach using a microscope. Equivalent of ~2 micron size inclusion as determined has been detected. The inspection time for completing a single plate is about one minute, while it will take about one hour to accomplish the same using the microscope/grid inspection approach.

In addition to these embodiments, persons skilled in the art can see that numerous modifications and changes may be made to the above invention without departing from the intended spirit and scope thereof.

I claim:

1. An apparatus for detecting inclusions in a transparent sheet, said sheet having a horizontal axis, at least one exterior surface parallel to said horizontal axis, at least one exterior surface not parallel to said horizontal axis, and a body defined by said exterior surfaces parallel and not parallel to said horizontal axis, said apparatus comprising:
   i. a laser source providing a primary collimated laser beam;
   ii. at least one light trap positioned on said at least one exterior surface parallel to said horizontal axis of the sheet; and
   iii. at least one detector positioned at an angle relative to the horizontal axis; and
   iv. a microprocessor to determine from the detected result of the detector presence and/or absence and/or location of inclusions in said transparent sheet, wherein,
   said at least one light trap blocks the primary beam of light and prevents it from illuminating said at least one exterior surface parallel to said horizontal axis of the sheet;
   said collimated laser beam enters into the sheet in a direction substantially parallel to the horizontal axis through said at least one surface not parallel to the horizontal axis into the body of the sheet, travels through the body of the sheet, and
   where there is an inclusion existing in the body of the sheet, said inclusion intercepts the primary incident beam of light, scatters the light and creates a secondary radiation source, and
   said at least one detector detects the secondary scattered light, and said apparatus has a sensitivity such that it can detect inclusions of less than or equal to 5 micrometers in size in the sheet.

2. An apparatus according to claim 1 having a sensitivity such that it can detect inclusions of less than or equal to 2 micrometers in size in the sheet.

3. An apparatus according to claim 2, wherein the angle of the detector relative to the horizontal axis is about 90 degrees.

4. An apparatus according to claim 2, wherein the transparent sheet has two exterior surfaces parallel to said horizontal axis and the apparatus has two of the light traps that prevent the primary light beam from illuminating the exterior surface parallel to said horizontal axis of the transparent sheet.

5. An apparatus according to claim 2, wherein the detector is a photo diode.

6. An apparatus according to claim 2, wherein the detector is a two dimensional CCD array.

7. An apparatus according to claim 2, wherein the light trap is made of opaque material having low reflective surface.

8. An apparatus according to claim 7, wherein the low reflective surface is made of black colored rubber.

9. An apparatus according to claim 1, wherein the angle of the detector relative to the horizontal axis is about 90 degrees.

10. An apparatus according to claim 1, wherein the transparent sheet has two exterior surfaces parallel to said horizontal axis and the apparatus has two of the light traps that prevent the primary light beam from illuminating the exterior surface parallel to said horizontal axis of the transparent sheet.

11. An apparatus according to claim 1, wherein the detector is a photo diode.

12. An apparatus according to claim 1, wherein the detector is a two dimensional CCD array.

13. An apparatus according to claim 1, wherein the light trap is made of opaque material having low reflective surface.

14. An apparatus according to claim 13, wherein the low reflective surface is made of black colored rubber.

15. Use of the apparatus according to claim 1 in detecting inclusions in transparent sheets made of materials comprising plastic, glass or high purity fused silica.

16. Use according to claim 15 of the apparatus, wherein the apparatus has a sensitivity such that it can detect inclusions of less than or equal to 2 micrometers in size in the sheet.

17. A process for detecting inclusions of less than or equal to 5 micrometers in size in a transparent sheet, said sheet having a horizontal axis, at least one exterior surface parallel to said horizontal axis, at least one exterior surface not parallel to said horizontal axis, and a body defined by said exterior surfaces parallel and not parallel to said horizontal axis, comprising:

i. Providing a collimated laser beam;

ii. Providing at least one light trap positioned on said at least one exterior surface parallel to the horizontal axis to block the primary beam of light and prevent it from illuminating said at least one exterior surface parallel to said horizontal axis of the sheet;

iii. Projecting said collimated laser beam in a direction substantially parallel to the horizontal axis through said at least one surface not parallel to said horizontal axis into said body of the sheet;

iv. Passing the collimated laser beam through said body as a whole at one time or by scanning different parts thereof sequentially;

v. Providing at least one detector positioned at an angel relative to said horizontal axis of the sheet to detect secondary light scattered by inclusions in the sheet;

vi. Determining the presence and/or absence and/or location of the inclusion of less than or equal to 5 micrometers in size from the detection result of secondary scattered light by the at least one detector.

18. A process according to claim 17 which can be used for detecting inclusions of less than or equal to 2 micrometers in size in a transparent sheet.

19. Use of the process according to claim 17 in detecting inclusions in transparent sheets made of materials comprising plastic, glass or high purity fused silica.

20. Use according to claim 19 of the process, wherein the process used has a sensitivity such that it can detect inclusions of less than or equal to 2 micrometers in size in the sheet.

* * * * *